US012758510B2

(12) United States Patent
Nishimura

(10) Patent No.: US 12,758,510 B2
(45) Date of Patent: Oct. 13, 2026

(54) PROPHYLACTIC AGENT, AMELIORATING AGENT, AND THERAPEUTIC AGENT FOR DRY EYE

(71) Applicant: Tsubota Laboratory, Inc., Tokyo (JP)

(72) Inventor: Emi Nishimura, Tokyo (JP)

(73) Assignee: TSUBOTA LABORATORY, INC., Tokyo (JP)

(*) Notice: Subject to any disclaimer, the term of this patent is extended or adjusted under 35 U.S.C. 154(b) by 571 days.

(21) Appl. No.: 18/246,508

(22) PCT Filed: Sep. 24, 2021

(86) PCT No.: PCT/JP2021/035110
§ 371 (c)(1),
(2) Date: Mar. 23, 2023

(87) PCT Pub. No.: WO2022/065436
PCT Pub. Date: Mar. 31, 2022

(65) Prior Publication Data

US 2023/0338307 A1 Oct. 26, 2023

(30) Foreign Application Priority Data

Sep. 25, 2020 (JP) ................................ 2020-160861

(51) Int. Cl.
*A61K 31/12* (2006.01)
*A61K 9/00* (2006.01)
*A61P 27/04* (2006.01)

(52) U.S. Cl.
CPC ............ *A61K 31/12* (2013.01); *A61K 9/0048* (2013.01); *A61P 27/04* (2018.01)

(58) Field of Classification Search
CPC ........ A61K 9/0048; A61K 31/12; A61P 27/04
See application file for complete search history.

(56) References Cited

U.S. PATENT DOCUMENTS 10,058,517 B1* 8/2018 Seyfang ............... C12N 15/101
2015/0139973 A1* 5/2015 Steinfeld ................ A61K 45/06 514/474
2016/0122406 A1* 5/2016 Coy ....................... A61K 45/06 514/17.7

FOREIGN PATENT DOCUMENTS

CN 101772344 7/2010
JP 2008-531697 A 8/2008
(Continued)

OTHER PUBLICATIONS

"Dry Eye disease and oxidative stress" review article; Seen et al; Act Opthalmologica; 2018; 96; p. e412-e420. (Year: 2018).*
(Continued)

*Primary Examiner* — Bethany P Barham
(74) *Attorney, Agent, or Firm* — Kilpatrick Townsend & Stockton LLP

(57) ABSTRACT

The present disclosure pertains to provision of: a tear layer stabilizer; a prophylactic agent, ameliorating agent, and therapeutic agent for corneal epithelial disorders; a prophylactic agent, ameliorating agent, and therapeutic agent for meibomian gland dysfunction; and a prophylactic agent, ameliorating agent, and therapeutic agent for dry eye. More specifically, provided are a tear layer stabilizer, a prophylactic agent, ameliorating agent, and therapeutic agent for corneal epithelial disorders, and a prophylactic agent, ameliorating agent, and therapeutic agent for meibomian gland dysfunction, and a prophylactic agent, ameliorating agent, and therapeutic agent for dry eye, each of which composition contains apocynin as an active ingredient.

12 Claims, 9 Drawing Sheets

(56) References Cited

FOREIGN PATENT DOCUMENTS

| | | | |
|---|---|---|---|
| JP | 2011-156030 | A | 8/2011 |
| JP | 2015-521182 | A | 7/2015 |
| JP | 2019-210282 | A | 12/2019 |
| TW | 202011947 | | 4/2020 |
| WO | 2006093864 | | 9/2006 |

OTHER PUBLICATIONS

"Apocynin protext retina cells from ultraviolet radiation damage via inducing sirtuin 1"; Liu et al.; Journal of Drug Targeting; Sep. 2019; vol. 28; #3; p. 330-338 (Year: 2019).*

"The latest thinking on dry eye treatments" by Heidi Godman; Harvard Health; p. 1-5; Oct. 13, 2022.*

PCT/JP2021/035110; International Search Report and Written Opinion, with translation; dated Oct. 26, 2021; 9 pages.

TW110135562, "Search Report", Mar. 26, 2025, 8 pages.

Office Action for Chinese Patent Application No. 202180065818X, Apr. 10, 2025, 5 pp.

Gu, et al., "Involvement of NADPH oxidases in alkali burn-induced cornealinjury", International Journal of Molecular Medicine, vol. 38, pp. 75-82

Shi, et al., "Advanced Glycation End Jun. 12, 20132 Products Induce Human Corneal Epithelial Cells Apoptosis through Generation of Reactive Oxygen Species and Activation of JNK and p38 MAPK Pathways", PLoS One, vol. 8, No. 6, e66781, pp. 1-10.

Borkar et al. Support Care Cancer 21:1167-1174 (2013).

Kojima et al. Progress in Retinal and Eye Research, p. 100842, 2020.

Lin et al. Mol Vis 17:257-264 (2011).

Yang et al. Int J Mol Med 41:1427-1436 (2018).

* cited by examiner

PROPHYLACTIC AGENT, AMELIORATING AGENT, AND THERAPEUTIC AGENT FOR DRY EYE

TECHNICAL FIELD

The present invention relates to a tear film stabilizing agent, a therapeutic agent for corneal epithelial disorders, and a prophylactic agent, an ameliorating agent and a therapeutic agent for meibomian gland dysfunction, as well as a prophylactic agent, an ameliorating agent and a therapeutic agent for dry eye.

BACKGROUND ART

Dry eye is a disease or symptom that develops into a chronic state with damage to the cornea and conjunctiva on the surface of the eye, resulting in dryness, discomfort, and visual function abnormalities due to abnormalities in the amount and composition of tears based on various factors. It is said that people receive more than 80% of their information through their eyes, and dry eye, which causes chronic eye symptoms, restricts behavior, lowers motivation, and reduces QOL (Non-patent Document 1).

Dry eye is a highly prevalent disease or condition. In recent years, due to the spread of air conditioning and the increase in VDT (visual display terminals) workers, etc., the number of dry eye patients has increased rapidly, reaching 8 million people in Japan and over 90 million people worldwide, and there is a growing medical need. In addition, it has been reported that the prevalence in Asia including Japan is higher than in Europe and the United States.

Furthermore, it is anticipated the number of complainants due to aging, wearing of contact lenses, and long hours of computer work, which are risk factors for dry eye, will continue to increase in the future. It is said that the act of continuously looking at a monitor screen makes it easier for tears to dry, causing eye strain and leading to a decline in visual function called evening presbyopia. There is a wide range of other causes for dry eye, and it is known to occur as a side effect of anticancer drug treatment. In particular, anticancer drugs are thought to affect corneal cells in which cell division is active, and dry eye is positioned as a side effect frequently seen with many molecular targeted drugs (Non-patent Document 2).

In dry eye, it is said that deterioration of the tear film stability is one of the core mechanisms, and corneal and conjunctival epithelial disorders become prominent in the process of becoming chronic and severe, resulting in various subjective symptoms. Dry eye is classified into the tear-deficient type and the evaporative type according to its cause. Meibomian gland dysfunction (MGD) is considered to be the cause of the evaporative type dry eye, and MGD is the cause in a significant proportion of patients who visit ophthalmology with dry eye symptoms such as ocular discomfort (Non-patent Document 1). In dry eye with a short tear film break-up time (BUT), characteristically the tear film break-up time is shortened, but the tear secretion is normal and the epithelial damage on the ocular surface is mild, considering that the subjective symptoms are strong.

Destruction (destabilization) of the tear film is caused by an abnormality in the tear lipid layer, a decrease in the water content of the tear film, an abnormality in the secretory mucin, or a decrease in the wettability of the epithelium. Currently, in Japan, the mainstream dry eye treatment is to compensate for the lack of ocular surface components as the cause of the destruction of the tear film that induces dry eye.

Specifically, artificial tears, sodium hyaluronate ophthalmic solution, rebamipide, diquafosol sodium, etc., which have an effect of promoting the secretion of mucin on the ocular surface, are used. While these ingredients promote the production of mucin and water and have the effect of stabilizing the tear film, it has been reported that diquafosol sodium causes ocular discharge and eye pain, and rebamipide causes dysgeusia as a side effect specific to ingredients. In addition, cyclosporine, which is used for severe dry eye, has many side effects, and a safer and more effective treatment for dry eye is desired.

The meibomian gland is a sebaceous gland that is located in the tarsal plate and has openings on the upper and lower eyelid margins. Lipids secreted by the meibomian gland are distributed in the eyelid margin and the outermost layer of the tear, and they work to inhibit tear evaporation, promote tear stability, promote the spreading of tears onto the ocular surface, suppress the outflow of tears at the eyelid margin to the skin and such.

MGD is clinically used to describe a condition in which the meibomian gland function is abnormal, and is thought to be one of the causes for the evaporative type dry eye, but its definitions and diagnostic criteria are still unclear due to the wide range of severity and diversity of clinical presentations. For these reasons, there are few effective treatments to date.

As described above, dry eye is a chronic eye disease that forms a vicious cycle in which corneal epithelial disorders and meibomian gland dysfunction influence and encourage each other, with destabilization of the tear film as one of the core mechanisms. Although stratified treatment of the ocular surface has been proposed to treat dry eye by increasing the stability of the tear film through supplementing the deficient components of the ocular surface, agents effective only in some layers are insufficient. There is a need for therapeutic agents that are pleiotropically effective against the core mechanisms of dry eye.

On the other hand, it has not been described or suggested that apocynin has a stabilizing effect on the tear film, a therapeutic effect on corneal epithelial disorders, or a therapeutic effect on meibomian gland dysfunction. Moreover, its action as a prophylactic agent, an ameliorating agent or a therapeutic agent for dry eye is not known at all.

CITATION LIST

Non-Patent Documents

Non-patent Document 1: Kojima et al. Progress in Retinal and Eye Research, p. 100842, 2020

Non-patent Document 2: Borkar et al. Support Care Cancer 21:1167-1174(2013)

Non-patent Document 3: Yang et al. Int J Mol Med 41:1427-1436 (2018)

Non-patent Document 4: Lin et al. Mol Vis 17:257-264 (2011)

SUMMARY OF THE INVENTION

Problems to be Solved by the Invention

The present invention has been made in view of the above circumstances, and an objective of the present invention is to provide a prophylactic agent, an ameliorating agent, or a therapeutic agent for dry eye that is excellent in the effect of stabilizing tear film, effect of treating corneal epithelial disorders, and effect of treating meibomian gland dysfunction.

Means for Solving the Problems

The present inventors have made intensive studies to achieve the above objective, and they found that apocynin is excellent in the effect of stabilizing tear film, effect of treating corneal epithelial disorders, and effect of treating meibomian gland dysfunction, and is useful as a prophylactic agent, an ameliorating agent, or a therapeutic agent for dry eye, and have thereby completed the present invention.

Therefore, the present invention provides the agents below.

Embodiment 1

A tear film stabilizing agent comprising apocynin.

Embodiment 2

A therapeutic agent for a corneal epithelial disorder comprising apocynin.

Embodiment 3

A therapeutic agent for meibomian gland dysfunction comprising apocynin.

Embodiment 4

A prophylactic agent, an ameliorating agent or a therapeutic agent for dry eye comprising apocynin.

Embodiment 5

The agent according to any one of embodiments 1 to 3, which is a prophylactic agent, an ameliorating agent or a therapeutic agent for dry eye.

Embodiment 6

The agent according to embodiment 4 or 5, which is a prophylactic agent, an ameliorating agent or a therapeutic agent for tear-deficient type dry eye.

Embodiment 7

The agent according to embodiment 4 or 5, which is a prophylactic agent, an ameliorating agent or a therapeutic agent for evaporative type dry eye.

Embodiment 8

The agent according to embodiment 4 or 5, which is a prophylactic agent, an ameliorating agent or a therapeutic agent for short-BUT type dry eye.

Embodiment 9

The agent according to embodiment 1, which is a prophylactic agent, an ameliorating agent or a therapeutic agent for a disease or symptom due to destabilization of the tear film selected from the group consisting of diseases or symptoms of eye fatigue, eye strain, eye dryness, blurred vision, eye pain, eye dazzles, heavy eye, eye discomfort, ocular discharge, lacrimation, hypolacrimation, age-related dry eye, alacrima, dry eye syndrome, Sjögren's syndrome, keratoconjunctivitis sicca, Stevens-Johnson syndrome, ocular pemphigoid, blepharitis, insufficiency of eye closure, sensory nerve paralysis, dry eye, tear-deficient type dry eye, evaporative type dry eye, short-BUT type dry eye, dry eye associated with allergic conjunctivitis, dry eye post viral conjunctivitis, dry eye post cataract surgery, dry eye associated with VDT work, dry eye associated with long period of staring at monitor screen, and dry eye associated with wearing contact lenses, as well as the group consisting of disorders or symptoms selected from discomfort while wearing contact lenses, lid wiper epitheliopathy, corneal and conjunctival epithelial disorders, corneal epithelial detachment, corneal epithelial erosion, corneal ulcers and eye infections.

Embodiment 10

The agent according to embodiment 2, which is a prophylactic agent, ameliorating agent or therapeutic agent for a disease or symptom due to a corneal epithelial disorder selected from the group consisting of eye fatigue, eye strain, eye dryness, blurred vision, eye pain, eye dazzles, heavy eye, eye discomfort, ocular discharge, lacrimation, corneal ulcers, corneal epithelial detachment, corneal inflammation, dry eye, tear-deficient type dry eye, evaporative type dry eye, short-BUT type dry eye, conjunctivitis, chronic superficial keratitis, corneal erosion, drug-induced corneal damage, persistent corneal damage, punctate superficial keratopathy, corneal epithelial defect, conjunctival epithelial defect, keratoconjunctivitis sicca, superior limbic keratoconjunctivitis, filamentary keratoconjunctivitis, infectious keratitis, non-infectious keratitis, infectious conjunctivitis, non-infectious conjunctivitis, corneal scarring or corneal scar formation as well as conjunctival scarring or conjunctival scar formation associated with keratoconjunctival disorder.

Embodiment 11

The agent according to embodiment 3, which is a prophylactic agent, ameliorating agent or therapeutic agent for a disease or symptom due to meibomian gland dysfunction selected from the group consisting of eye fatigue, eye strain, eye dryness, blurred vision, eye pain, eye dazzles, heavy eye, eye discomfort, burning sensation with hot eyelids, ocular discharge, lacrimation, dry eye, tear-deficient type dry eye, evaporative type dry eye, short-BUT type dry eye, meibomianitis, punctate superficial keratitis, and blepharitis.

Embodiment 12

The agent according to any one of embodiments 1 to 11, which is an eye drop or an eye ointment.

Embodiment 2-1

A method of stabilizing tear film, comprising administering a composition comprising apocynin as an active ingredient to a subject in need of treatment.

Embodiment 2-2

A method of treating a corneal epithelial disorder, comprising administering a composition comprising apocynin as an active ingredient to a subject in need of treatment.

Embodiment 2-3

A method of treating meibomian gland dysfunction, comprising administering a composition comprising apocynin as an active ingredient to a subject in need of treatment.

Embodiment 2-4

A method of preventing, ameliorating or treating dry eye, comprising administering a composition comprising apocynin as an active ingredient to a subject in need of treatment.

Embodiment 2-5

The method according to any one of embodiments 2-1 to 2-3, which is a method for preventing, ameliorating or treating dry eye.

Embodiment 2-6

The method according to embodiment 2-4 or 2-5, which is a method for preventing, ameliorating or treating tear-deficient type dry eye.

Embodiment 2-7

The method according to embodiment 2-4 or 2-5, which is a method for preventing, ameliorating or treating evaporative type dry eye.

Embodiment 2-8

The method according to embodiment 2-4 or 2-5, which is a method for preventing, ameliorating or treating short-BUT type dry eye.

Embodiment 2-9

The method according to embodiment 2-1, which is a method for preventing, ameliorating or treating a disease or symptom due to destabilization of the tear film selected from the group consisting of diseases or symptoms of eye fatigue, eye strain, eye dryness, blurred vision, eye pain, eye dazzles, heavy eye, eye discomfort, ocular discharge, lacrimation, hypolacrimation, age-related dry eye, alacrima, dry eye syndrome, Sjögren's syndrome, keratoconjunctivitis sicca. Stevens-Johnson syndrome, ocular pemphigoid, blepharitis, insufficiency of eye closure, sensory nerve paralysis, dry eye, tear-deficient type dry eye, evaporative type dry eye, short-BUT type dry eye, dry eye associated with allergic conjunctivitis, dry eye post viral conjunctivitis, dry eye post cataract surgery, dry eye associated with VDT work, dry eye associated with long period of staring at monitor screen, and dry eye associated with wearing contact lenses, as well as the group consisting of disorders or symptoms selected from discomfort while wearing contact lenses, lid wiper epitheliopathy, corneal and conjunctival epithelial disorders, corneal epithelial detachment, corneal epithelial erosion, corneal ulcers and eye infections.

Embodiment 2-10

The method according to embodiment 2-2, which is a method for preventing, ameliorating or treating a disease or symptom due to a corneal epithelial disorder selected from the group consisting of eye fatigue, eye strain, eye dryness, blurred vision, eye pain, eye dazzles, heavy eye, eye discomfort, ocular discharge, lacrimation, corneal ulcers, corneal epithelial detachment, corneal inflammation, dry eye, tear-deficient type dry eye, evaporative type dry eye, short-BUT type dry eye, conjunctivitis, chronic superficial keratitis, corneal erosion, drug-induced corneal damage, persistent corneal damage, punctate superficial keratopathy, corneal epithelial defect, conjunctival epithelial defect, keratoconjunctivitis sicca, superior limbic keratoconjunctivitis, filamentary keratoconjunctivitis, infectious keratitis, non-infectious keratitis, infectious conjunctivitis, non-infectious conjunctivitis, corneal scarring or corneal scar formation as well as conjunctival scarring or conjunctival scar formation associated with keratoconjunctival disorder.

Embodiment 2-11

The method according to embodiment 2-3, which is a method for preventing, ameliorating or treating a disease or symptom due to meibomian gland dysfunction selected from the group consisting of eye fatigue, eye strain, eye dryness, blurred vision, eye pain, eye dazzles, heavy eye, eye discomfort, burning sensation with hot eyelids, ocular discharge, lacrimation, dry eye, tear-deficient type dry eye, evaporative type dry eye, short-BUT type dry eye, meibomianitis, punctate superficial keratitis, and blepharitis.

Embodiment 2-12

The method according to any one of embodiments 2-1 to 2-11, wherein the composition is an eye drop or eye ointment.

Embodiment 3-1

A pharmaceutical composition for use in stabilizing tear film, comprising apocynin as an active ingredient.

Embodiment 3-2

A pharmaceutical composition for use in treating a corneal epithelial disorder, comprising apocynin as an active ingredient.

Embodiment 3-3

A pharmaceutical composition for use in treating meibomian gland dysfunction, comprising apocynin as an active ingredient.

Embodiment 3-4

A pharmaceutical composition for use in preventing, ameliorating or preventing dry eye, comprising apocynin as an active ingredient.

Embodiment 3-5

The pharmaceutical composition according to any one of embodiments 3-1 to 3-3, which is for use in preventing, ameliorating or preventing dry eye.

Embodiment 3-6

The pharmaceutical composition according to embodiment 3-4 or 3-5, which is for use in preventing, ameliorating or preventing tear-deficient type dry eye.

Embodiment 3-7

The pharmaceutical composition according to embodiment 3-4 or 3-5, which is for use in preventing, ameliorating or preventing evaporative type dry eye.

Embodiment 3-8

The pharmaceutical composition according to embodiment 3-4 or 3-5, which is for use in preventing, ameliorating or preventing dry eye.

Embodiment 3-9

The pharmaceutical composition according to embodiment 3-1, which is for use in preventing, ameliorating or treating a disease or symptom due to destabilization of the tear film selected from the group consisting of diseases or symptoms of eye fatigue, eye strain, eye dryness, blurred vision, eye pain, eye dazzles, heavy eye, eye discomfort, ocular discharge, lacrimation, hypolacrimation, age-related dry eye, alacrima, dry eye syndrome, Sjögren's syndrome, keratoconjunctivitis sicca, Stevens-Johnson syndrome, ocular pemphigoid, blepharitis, insufficiency of eye closure, sensory nerve paralysis, dry eye, tear-deficient type dry eye, evaporative type dry eye, short-BUT type dry eye, dry eye associated with allergic conjunctivitis, dry eye post viral conjunctivitis, dry eye post cataract surgery, dry eye associated with VDT work, dry eye associated with long period of staring at monitor screen, and dry eye associated with wearing contact lenses, as well as the group consisting of disorders or symptoms selected from discomfort while wearing contact lenses, lid wiper epitheliopathy, corneal and conjunctival epithelial disorders, corneal epithelial detachment, corneal epithelial erosion, corneal ulcers and eye infections.

Embodiment 3-10

The pharmaceutical composition according to embodiment 3-2, which is for use in preventing, ameliorating or treating a disease or symptom due to a corneal epithelial disorder selected from the group consisting of eye fatigue, eye strain, eye dryness, blurred vision, eye pain, eye dazzles, heavy eye, eye discomfort, ocular discharge, lacrimation, corneal ulcers, corneal epithelial detachment, corneal inflammation, dry eye, tear-deficient type dry eye, evaporative type dry eye, short-BUT type dry eye, conjunctivitis, chronic superficial keratitis, corneal erosion, drug-induced corneal damage, persistent corneal damage, punctate superficial keratopathy, corneal epithelial defect, conjunctival epithelial defect, keratoconjunctivitis sicca, superior limbic keratoconjunctivitis, filamentary keratoconjunctivitis, infectious keratitis, non-infectious keratitis, infectious conjunctivitis, non-infectious conjunctivitis, corneal scarring or corneal scar formation as well as conjunctival scarring or conjunctival scar formation associated with keratoconjunctival disorder.

Embodiment 3-11

The pharmaceutical composition according to embodiment 3-3, which is for use in preventing, ameliorating or treating a disease or symptom due to meibomian gland dysfunction selected from the group consisting of eye fatigue, eye strain, eye dryness, blurred vision, eye pain, eye dazzles, heavy eye, eye discomfort, burning sensation with hot eyelids, ocular discharge, lacrimation, dry eye, tear-deficient type dry eye, evaporative type dry eye, short-BUT type dry eye, meibomianitis, punctate superficial keratitis, and blepharitis.

Embodiment 3-12

The pharmaceutical composition according to any one of embodiments 3-1 to 3-11, wherein the composition is an eye drop or eye ointment.

Effect of the Invention

According to the present invention, it is possible to provide tear film stabilizing agents, corneal epithelial disorder treatment agents, and meibomian gland dysfunction treatment agents that excel in the effect of stabilizing tear film, effect of treating corneal epithelial disorders, and effect of treating meibomian gland dysfunction, which are useful as prophylactic agents, ameliorating agents, or therapeutic agents for dry eye.

MODE FOR CARRYING OUT THE INVENTION

Figure 1:
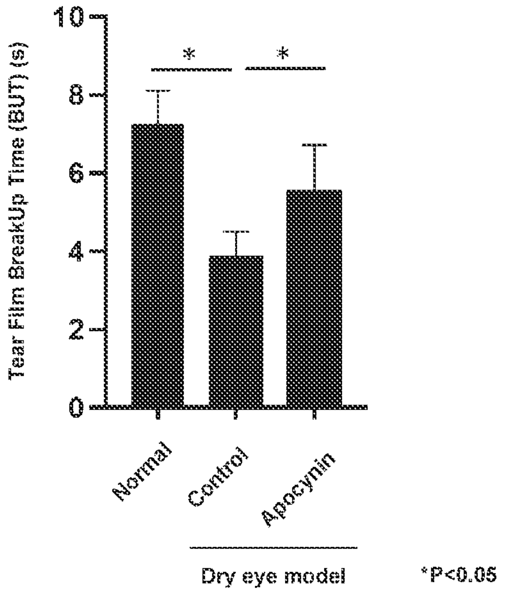
FIG. 1 It is a graph that demonstrates the results of tear film breakup time (BUT) in the dry eye model of Example 1. All error bars in the graph indicate S.D. (standard deviation).

Hereinbelow, the present invention will be explained in detail.

Apocynin

Apocynin is 4-hydroxy-3-methoxyacetophenone and has the formula below. Apocynin can be produced by a known method, and commercially available products can also be used.

Formula I

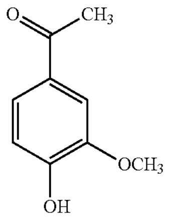

This product can be formulated as an ophthalmic drug comprising two or more active ingredients by mixing other active ingredients and pharmaceutically acceptable additives in addition to apocynin, using a commonly applied technique, or it can be formulated as an ophthalmic drug comprising apocynin alone as an active ingredient by adding a pharmaceutically acceptable additive to apocynin, using a commonly applied technique.

In the present invention, this drug is administered topically to the eye. Examples of dosage forms of this drug include eye drop administration (including application of eye ointment and eye wash), subconjunctival administration, intraconjunctival sac administration, and subtenon administration, and eye drop administration is particularly preferred.

The dosage form of this drug is not particularly limited as long as it is used for topical administration to the eye. Examples include eye drops, eye ointments, injections, patches, gels, and inserts. In addition, these can be prepared using the general techniques widely used in the field.

Eye drops are prepared using isotonic agents such as sodium chloride, potassium chloride, and concentrated glycerin; buffering agents such as sodium phosphate, sodium acetate and epsilon-aminocaproic acid; surfactants such as polyoxyethylene sorbitan monooleate, polyoxyl 40 stearate and polyoxyethylene hardened castor oil; stabilizers such as sodium citrate and sodium edetate; and preservatives such as parabens, which are selected for use as needed. The pH should be within the range acceptable for ophthalmic preparations, but usually 4-8 is preferred.

Eye ointments can be prepared using commonly used bases such as white petrolatum and liquid paraffin.

Other Ingredients

The agents (compositions) of the present invention can contain an appropriate amount of other ingredients within a range that does not impair the effects of the present invention. Other ingredients include water, oily ingredients, surfactants, preservatives, sugars, buffers, pH adjusters, isotonic agents, stabilizers, cooling agents, polyhydric alcohols, thickeners, and such. These components can be blended singly or in combination of two or more. The amount of water can be the remaining portion of the composition.

When the pharmaceutical composition of the present invention is an eye drop, the content of the active ingredient apocynin is, for example, as a lower limit of at least 0.00001% (w/v), at least 0.0001% (w/v), at least 0.001% (w/v)), at least 0.01% (w/v), at least 0.003% (w/v), at least 0.03% (w/v), or at least 0.1% (w/v), and as an upper limit of 1% (w/v) or less, 0.1% (w/v) or less, 0.03% (w/v) or less, 0.01% (w/v) or less, 0.003% (w/v) or less, 0.001% (w/v) or less, or 0.0001% (w/v) or less. The range is defined by any combination of these lower and upper limits, for example, 0.00001% (w/v) to 1% (w/v), 0.0001% (w/v) to 0.1% (w/v), 0.003% (w/v) to 0.03% (w/v), 0.003% (w/v) to 0.1% (w/v) or 0.001% (w/v) to 0.01% (w/v). As one embodiment of the present invention, the eye drop has an active ingredient content of 0.001% (w/v), 0.003% (w/v), 0.005% (w/v) or 0.01% (w/v), 0.03% (w/v), 0.1% (w/v). Note that "w/v" represents weight/volume.

When used as an eye drop, it is applied preferably with 10 to 100 μL of 1 to 3 drops at a time, 1 to 6 times a day, more preferably with 10 to 50 μL of 1 to 6 drops at a time, 1 to 6 times a day, and even more preferably with 10 to 30 μL of 1 to 3 drops at a time, 1 to 6 times a day. The administration method of the pharmaceutical composition of the present invention may be appropriately determined according to the patient's body weight, age, sex, degree of disease, and the like. In the case of eye drops, the regimen in adults is, for example, 1 drop per eye, administered 1 to 6 times daily. The administration interval can be determined appropriately, and for example, it can be 3 to 4 hours.

The agent of the present invention can be suitably used as eye drops, eye drops for contact lenses, eye washes, etc. From the point of view of its effectiveness in dry eye prevention, amelioration or treatment, it can be suitably used as eye drops, eye drops for contact lenses (eye drops for contact lens wearers) or other eye drops. Contact lenses include hard contact lenses, soft contact lenses, silicone hydrogel soft contact lenses, O2 hard contact lenses, color contact lenses, and others, and are not particularly limited.

In addition, after filling the obtained agent (composition) in a resin container, it is further sealed with a package, and an inert gas such as nitrogen is sealed in the space formed between the above-mentioned container and the package. Alternatively, after the composition is filled in a resin container, it may be sealed within a package together with an oxygen scavenger.

This drug is intended to be administered to treat dry eye symptoms, but it may also be locally administered to the eye prophylactically before dry eye symptoms develop.

One embodiment of the present invention relates to a method for treating, ameliorating, or preventing dry eye and the diseases or symptoms described in the present disclosure, comprising administering to a patient a composition comprising apocynin as an active ingredient. Moreover, one embodiment of the present invention relates to the use of apocynin in the treatment, amelioration or prevention of dry eye and the diseases or conditions described in the present disclosure. In addition, one embodiment of the present invention relates to the use of apocynin in the manufacture of a medicament for the treatment, amelioration or prevention of dry eye and the diseases or conditions described in the present disclosure.

Dry Eye

Dry eye is defined as "a disease in which the stability of the tear film decreases due to various factors, causing ocular discomfort and abnormal visual function, and may be accompanied by damage to the ocular surface".

Dry eye is broadly classified into two types according to etiology: "tear-deficient type" and "evaporative type" (Non-patent Document 1).

Tear-deficient dry eye reduces the production of tear fluid, damages the surface of the eye, and causes symptoms such as constant dryness and foreign body sensation. The causes include aging, stress, graft-versus-host disease (GVHD), Sjögren's syndrome, tear secretion deficiency due to oral anticholinergic drugs, and lacrimal gland conduit obstruction due to inflammatory ocular surface diseases such as Stevens-Johnson syndrome or pemphigoid ophthalmicus, and impediment of the reflex tear pathway (reflex loop) due to β-blockers, surgery, and such. Recently, a relationship between increased VDT work hours and decreased lacrimal gland function has been reported, suggesting that the living environment and lifestyle affect lacrimal secretion.

The causes of evaporative dry eye are classified into intrinsic and extrinsic factors. Extrinsic factors include vitamin A deficiency, preservatives in eye drops (e.g., benzalkonium chloride), allergic conjunctivitis, use of contact lenses, and air conditioning. Intrinsic factors include MGD, eyelid abnormalities such as rabbit eyes, and decreased number of blinks.

In short-BUT dry eye, the BUT is shortened, lachrymal secretion is normal, and epithelial damage on the ocular surface is mild, but severe symptoms are produced such as eye fatigue, eye dryness, discomfort when wearing contact lenses, blurred vision, foreign body sensation, eye pain, eye dazzles, heavy eye, eye discomfort, ocular discharge and lacrimation. Conventionally used artificial tears and hyaluronic acid have poor therapeutic effects.

In dry eye, when the stability of the tear film decreases due to various upstream risk factors, corneal and conjunctival epithelial damage occurs due to drying stress, resulting in damage to the mucin on the epithelial surface and reduced water wettability. As a result, a vicious circle (core mechanism) occurs in which the stability of the tear film is further reduced. Furthermore, this vicious circle results in inflammation, which promotes epithelial damage. More recently, it has been proposed that symptoms are caused by two mechanisms: a vicious circle of "decreased tear film stability" when eyelids are kept open, and a vicious circle of "increased friction" when blinking. This is due to the stability of tear fluid, which prevents the ocular surface from drying out, and its role as a lubricant to prevent excessive friction. As background information, the vicious circle of "increased friction" during blinking is caused by the interaction between the eyelid conjunctival epithelium and the ocular surface epithelium (rubbing against each other via tear fluid) during blinking, resulting in a decrease in the water content of the tear fluid and a decrease or qualitative abnormality in secretory or membrane-type mucins. It is also known that meibomian gland dysfunction (MGD) occurs in many patients with dry eye because the oils and fats that come from the meibomian glands prevent tear evaporation. As described above, dry eye is a chronic eye disease in which tear film instability is one of the core mechanisms, and corneal epithelial disorder and meibomian gland dysfunction influence and encourage each other, thereby forming a vicious circle, and this makes symptomatic treatment alone by targeting inflammation or such insufficient.

Anti-inflammatory drugs such as corticosteroids and cyclosporin are used for treatment of dry eye caused by collagen diseases related to autoimmunity such as Sjögren's syndrome. Although corticosteroid eye drops have been proposed as a treatment option because they improve subjective symptoms of dry eye, there is no evidence that they are effective against tear stability. Although it is used infrequently, the possibility that it may cause an increase in intraocular pressure and affect visual function cannot be ruled out, and its use should be carefully monitored. There is no evidence that non-steroidal anti-inflammatory drug (NSAID) eye drops are effective in improving subjective symptoms, tear stability, or epithelial damage, while corneal hypersensitivity is sometimes observed as an adverse event, and thus they are not practiced as a treatment option. In addition, oral administration of common antioxidants and eye drops has not been proven to be sufficiently effective for dry eye.

Dry eye is a chronic eye disease that may also involve systemic factors. Dry eye associated with collagen disease is caused by autoimmune damage to the corneal conjunctival epithelium, which leads to inflammation and destabilization of the tear film. On the other hand, diabetic retinopathy and ischemic retinopathy are often associated with the so-called lifestyle-related diseases such as diabetes, arteriosclerosis, and hypertension, but because they are caused by ischemia in blood vessels, treatment such as retinal photocoagulation is used, and little is known about their relationship to dry eye. Dry eye also increases with age, but it is thought to have little association with cataracts, glaucoma, retinal detachment, or other ocular diseases.

The outcome that should be considered in the treatment of dry eye patients with either the tear-deficient type, the evaporative type, or the short-BUT type is the reduction of subjective symptoms. These are prolongation of the break-up time (BUT), alleviation of reduction of tear volume, and reduction of corneal epithelial damage.

The apocynin of the present invention elongates BUT, alleviates tear volume reduction, and demonstrates a therapeutic effect on corneal epithelial disorders and a therapeutic effect on meibomian gland dysfunction, based on its effect of stabilizing the tear film. It can show remarkable prophylactic, ameliorating or therapeutic effects on any types of dry eyes, whether it be the tear-deficient type, evaporative type, or short-BUT type dry eye.

Tear Film Stabilizing Agents

The present invention is a tear film stabilizing agent comprising apocynin, preferably a tear film stabilizing agent comprising apocynin as an active ingredient.

In the present invention, the tear film stabilizing effect is measured by fluorescein BUT or Schirmer test. Specifically, it is the method in the Example described below.

Once the stabilizing effect of the tear film is obtained, the agent can be suitably used as a prophylactic, ameliorating, or therapeutic agent for dry eye, tear-deficient type, evaporative type, or short-BUT type dry eye, in which instability of the tear film is one of the core mechanisms. The tear film stabilizing agent of the present invention may be used with or without an increase in the volume of tear secretion, and even without an increase in tear secretion volume, it can show a remarkable prophylactic or therapeutic effect for dry eye. Thus, one aspect of the present invention relates to a prophylactic, ameliorating, or therapeutic agent for dry eye, for example, tear-deficient type dry eye, evaporative type dry eye, and short-BUT type dry eye, comprising apocynin as an active ingredient.

The following symptoms are listed as diseases or symptoms caused by destabilization of the tear film, and the tear film stabilizing agent of the present invention can be suitably used as a prophylactic agent, an ameliorating agent or a therapeutic agent for the diseases or symptoms below.

Therefore, some aspects of the present invention are suitable for use as a prophylactic agent, an ameliorating agent, or a therapeutic agent for the following diseases or symptoms caused by tear film instability: eye fatigue, eye strain, eye dryness, blurred vision, eye pain, eye dazzles, heavy eye, eye discomfort, ocular discharge, lacrimation, hypolacrimation, age-related dry eye, alacrima, dry eye syndrome, Sjögren's syndrome, keratoconjunctivitis sicca, Stevens-Johnson syndrome, ocular pemphigoid, blepharitis, insufficiency of eye closure, sensory nerve paralysis, dry eye, tear-deficient type dry eye, evaporative type dry eye, short-BUT type dry eye, dry eye associated with allergic conjunctivitis, dry eye post viral conjunctivitis, dry eye post cataract surgery, dry eye associated with VDT work, dry eye associated with long period of staring at monitor screen such as smartphones and video games, and dry eye associated with wearing contact lenses, as well as the group consisting of disorders or symptoms selected from discomfort while wearing contact lenses, lid wiper epitheliopathy, corneal and conjunctival epithelial disorders, corneal epithelial detachment, corneal epithelial erosion, corneal ulcers and eye infections.

Therapeutic Agents for Corneal Epithelial Disorders

One aspect of the present invention is an agent for treating corneal epithelial disorders comprising apocynin, and it is preferred that the agent is an agent for treating corneal epithelial disorders comprising apocynin as an active ingredient.

In the present invention, the efficacy of corneal epithelial disorder treatment is measured by the fluorescein-stained image of the eye surface and the fluorescein staining score. Specifically, the method is described in the Example below.

Once a therapeutic effect on corneal epithelial damage is obtained, the product can be suitably used as a prophylactic agent, an ameliorating agent, or a therapeutic agent for dry eye.

The cornea is a transparent, avascular tissue with a diameter of about 1 cm that covers the front surface of the eyeball, and the conjunctiva is the mucous membrane that covers the surface of the eyeball behind the corneal limbus and the back surface of the eyelid. They play important functions in vision, and any disturbance has serious effects on visual function. Corneal and conjunctival disorders induced by dry eye are caused by external obstruction, delayed repair of the obstruction or spreading of the obstruction induced by some reasons. Since the cornea and conjunctiva are connected tissues, these diseases adversely affect the normal architecture of each other's epithelium, and they may even impair the structure and function of the corneal stroma and endothelium.

In dry eye, the corneal conjunctival epithelial damage becomes more pronounced as the disease becomes chronic and severe, with a decrease in tear film stability as one of the core mechanisms. Apocynin has an excellent therapeutic effect on the corneal epithelium and is useful as a prophylactic agent, an ameliorating agent, and a therapeutic agent for dry eye.

The drug-induced corneal epithelial disorder appears as a punctate superficial corneal layer similar to dry eye. Causative eye drops include sympatholytics and nonsteroidal anti-inflammatory drugs (NSAIDs), which reduce corneal sensitivity, and preservatives in eye drops, particularly benzalkonium chloride. Systemic drugs such as anticancer drugs, amiodarone, and isotretinoin also severely damage the cornea.

It has been reported that typical dry eye symptoms are actually induced by administering these drugs to mice (Non-patent Documents 2 and 3).

In the present invention, a keratoconjunctival disorder refers to conditions in which the cornea and conjunctiva are damaged due to various factors such as lacrimal abnormalities, metabolic disorders, and external obstacles. Examples include corneal ulcers, corneal epithelial detachment, corneal inflammation, dry eye, conjunctivitis, chronic superficial keratitis, corneal erosion, drug-induced corneal damage, persistent corneal damage, punctate superficial keratopathy, corneal epithelial defect, conjunctival epithelial defect, keratoconjunctivitis sicca, superior limbic keratoconjunctivitis, filamentary keratoconjunctivitis, infectious keratitis, non-infectious keratitis, infectious conjunctivitis, and non-infectious conjunctivitis. Further, in the present invention, corneal scarring (corneal scar formation) as well as conjunctival scarring (conjunctival scar formation) associated with keratoconjunctival disorder are also examples of the keratoconjunctival disorder.

Meibomian Gland Dysfunction Therapeutic Agent

One aspect of the present invention is a therapeutic agent for meibomian gland dysfunction comprising apocynin. One aspect of the present invention is a therapeutic agent for meibomian gland dysfunction comprising apocynin, preferably a therapeutic agent for meibomian gland dysfunction comprising apocynin as an active ingredient.

In the present invention, the therapeutic effect of meibomian gland dysfunction is determined based on the silhouette image of the meibomian glands. Specifically, the method is in the Example described below.

The meibomian glands present in the eyelids secrete lipids and are important as the source of supply for the lacrimal lipid layer. This tear lipid layer is important for lowering the surface tension of tears, preventing evaporation of tears, and stabilizing tears as a film. However, there are few reports on the secretory mechanism of the meibomian glands, and it has not been fully elucidated.

In the present invention, MOD is a condition in which the function of the meibomian glands is diffusely or locally abnormal due to various factors, and it is often accompanied by dry eye symptoms such as abnormalities of the tear fluid and ocular surface, chronic ocular discomfort (rattling, shaggy feeling, etc.). Symptoms of MGD include eye fatigue, eye strain, eye dryness, blurred vision, eye pain, eye dazzles, heavy eye, eye discomfort, burning sensation with hot eyelids, ocular discharge, lacrimation, and such. Furthermore, MGD may be accompanied by inflammatory diseases, and such MGD is also suitable for application of the present invention. The inflammatory diseases include, for example, meibomianitis, punctate superficial keratitis, and blepharitis.

In the treatment of MGD, hyperthermia and compression by applying physical force are performed to improve meibomian gland blockage. In recent years, methods have also been developed in which the tear lipid layer is evaluated using interference images, and the eyelid is treated from the inside using heat and massage effects. However, since all these methods require treatment within a medical institution, a simple treatment method is eagerly awaited.

MGD is broadly divided into the hyposecretory type and hypersecretory type, and the hyposecretory type is more frequent in clinical practice. MOD of the hyposecretory type are primary and can be obstructive, atrophic or congenital, with the obstructive type being the most common. In the obstructive type, excess keratinized material accumulates in the meibomian gland ducts, meibomian gland lipid secretion decreases, and atrophy of the meibomian gland acini progresses gradually. Atrophic refers to primary atrophy of the gland acini. In secondary atrophy, a variety of factors cause obstruction of the meibomian gland orifices, resulting in a decrease in the secretion of meibomian gland lipid. Contact lenses have also been reported to affect the morphology of meibomian glands and contribute to dry eye.

As used in the present disclosure, atrophy of meibomian glands refers to a state in which the volume of an organ or tissue that has grown to a normal volume has decreased due to various factors, and it may include total or partial atrophy of meibomian glands. As used in the present disclosure, atrophy of meibomian glands refers to atrophy of any of the parts that make up the meibomian glands, such as (but not limited to) secretory acini, small ducts, central ducts, and exit ducts, or a combination thereof. Examples of meibomian atrophy with decreased meibomian gland volume include, but are not limited to, atrophy due to shedding of glandular tissue, acinar loss, and decreased cell numbers. In a preferred embodiment of the invention, the meibomian gland dysfunction is accompanied by atrophy of the meibomian glands.

In other words, the agents used for specific medical uses described in the present disclosure can also be expressed as pharmaceutical compositions for specific medical uses, particularly for treatment of dry eye. Also, the agents or pharmaceutical compositions described in the present disclosure may be used in methods, particularly methods of treating dry eye, that include administering such compositions to a subject or patient in need thereof.

Although preferred embodiments of the present invention have been described in the present specification, it will be apparent to those skilled in the art that such embodiments are provided for illustrative purposes only, and various modifications, changes and substitutions could be made without departing from the invention by those skilled in the art. One should understand that various alternative embodiments of the present invention described herein may be used in practicing the invention. Further, it should be interpreted that the contents of all publications, including patents and patent applications, referenced herein are deemed to be incorporated by reference as if expressly set forth herein.

Although the present invention will be described in detail below using examples, the present invention is not limited to the examples below. In addition, the reagents and materials used are commercially available unless otherwise specified.

EXAMPLES

Example 1: Therapeutic Effects of Apocynin on Dry Eye Model Animals

After acclimating male C57BL6 mice (7 weeks old) to the experimental environment, those with almost uniform body weight values and no eye abnormalities were divided into the following 3 groups (n=5).

7 weeks old/normal (non-dry eye group)

7 weeks old/dry eye model+control (solvent eye drop) group 7 weeks old/dry eye model+apocynin eye drop group The dry eye model was created by daily instillation of an EGF receptor inhibitor (erlotinib) based on the method of Yang et al. In this model, administration of erlotinib causes dry eye symptoms such as shortened BUT, decreased tear volume, and corneal damage after 1 week of administration (Non-patent Document 3). After 20 μM of erlotinib was instilled for 2 weeks, the control group received PBS alone, and the test group received 3 μL of a suspension of 0.003% (w/v) apocynin in PBS twice daily. Two weeks after the start of instillation, 1 μL of 0.1% sodium fluorescein solution was instilled into each of both eyes under isoflurane anesthesia, and a BUT test was performed using a slit lamp (Kowa Co., Ltd., SL-17) (FIG. 1). In addition, the Schirmer test was used to evaluate tear volume. Under anesthesia, the tip of a Schirmer test paper cut to 1 mm width was inserted into the conjunctival sac of the lower eyelid of the mouse, the test paper was removed after 5 minutes, the length of the wetted part was read in units of 0.5 mm, and the value was used as the tear volume (FIG. 2).

Figure 2:
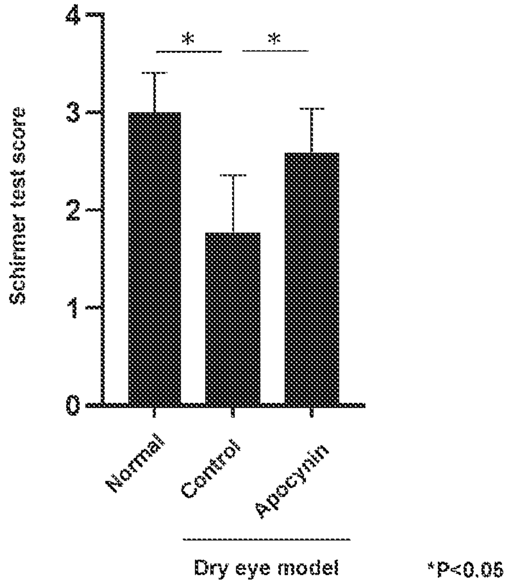
FIG. 2 It is a graph showing Schirmer test results in the dry eye model of Example 1. All error bars in the graph indicate S.D.

As shown in FIGS. 1 and 2, the apocynin eye drop group improved the shortening of BUT and the reduction of tear volume in the dry eye model, demonstrating that apocynin is useful as a tear film stabilizing agent.

Evaluation of Therapeutic Effects for Corneal Epithelial Disorders

Figure 3A:
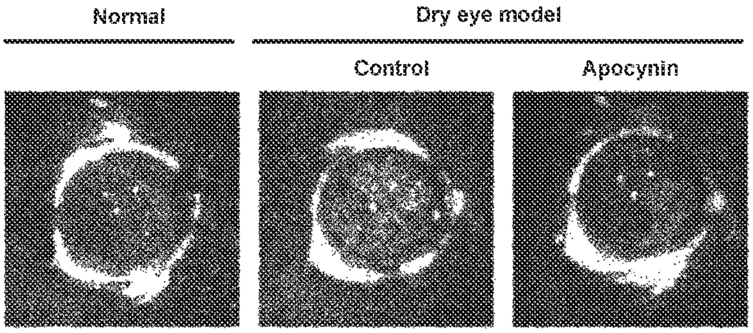
FIG. 3A It is a fluorescein-stained image of the dry eye model in Example 1.
Figure 3B:
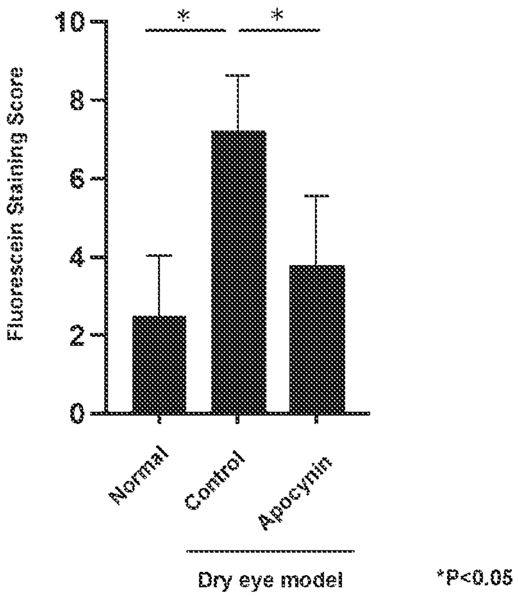
FIG. 3B It is a graph showing fluorescein staining scores in the dry eye model of Example 1. All error bars in the graph indicate S.D.

In the dry eye model prepared in Example 1, after BUT measurement, fluorescein-stained images were photographed under a blue filter using a slit lamp (Kowa Co., Ltd., SL-17), and corneal epithelial damage was analyzed (FIG. 3). The lesioned area of the cornea was stained by fluorescein staining. For the corneal damage score, the central part of the mouse eye was taken as one area, and the other area was divided into four equivalent regions, and each of the total five regions was scored from 0 to 3 points according to the degree of staining (15 points in total).

As shown in FIG. 3, significant improvement was observed in the apocynin eye drop group for the corneal epithelial damage that occurred in the dry eye model of Example 1, demonstrating that apocynin is useful as a therapeutic agent for corneal epithelial damage.

Example 2: Therapeutic Effects of Apocynin on the Dry Eye Model Animals

After acclimating male C57BL6 mice (9 weeks old) to the experimental environment, those with almost uniform weight values and no eye abnormalities were divided into the following 3 groups (n=3).

7 weeks old/normal (non-dry eye group)

7 weeks old/dry eye model+control (solvent eye drop) group 7 weeks old/dry eye model+apocynin eye drop group The dry eye model was created by instilling a 0.2% benzalkonium chloride solution based on the method of Lin et al. (Non-patent Document 4). In this model, instillation of the 0.2% benzalkonium chloride solution causes dry eye symptoms such as shortened BUT, decreased tear volume, and corneal epithelial damage after 1 day of administration (Non-patent Document 4). After the benzalkonium chloride solution was instilled twice daily for 2 days, PBS alone was administered to the control group, and for the test group, a solution of apocynin 0.003% (w/v) suspended in PBS was administered to both eyes at 3 μL each, 4 times daily. Two days after the start of apocynin instillation, 1 μL of 0.1% fluorescein sodium solution was instilled into each of both eyes under isoflurane anesthesia, and stained images were taken under a blue filter using a slit lamp (Kowa Co., Ltd., SL-17). The fluorescein staining scores were analyzed (FIG. 4).

Figure 4A:
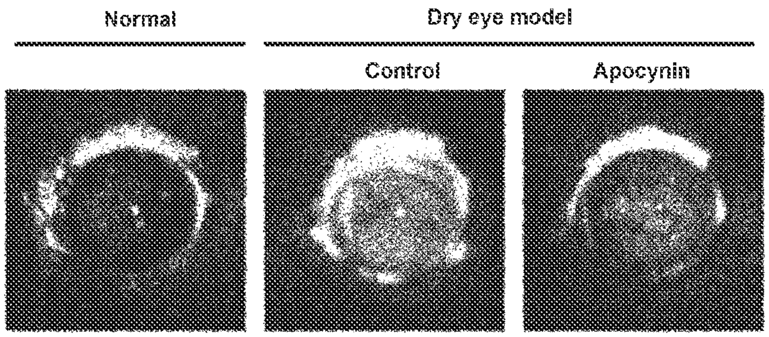
FIG. 4A It is a fluorescein-stained image of the dry eye model in Example 2.
Figure 4B:
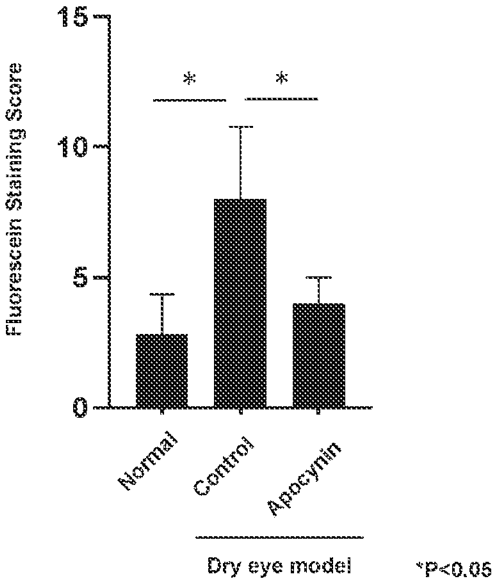
FIG. 4B It is a graph showing fluorescein staining scores in the dry eye model of Example 2. All error bars in the graph indicate S.D.

As shown in FIG. 4, corneal epithelial damage induced by the benzalkonium chloride solution was significantly improved in the apocynin eye drop group, and it was demonstrated that apocynin is also useful as a therapeutic agent for corneal epithelial damage in dry eye models induced by different drugs.

Example 3: Therapeutic Effects of Apocynin on Dry Eye Model Animals

After acclimating male C57BL6 mice (7 weeks old) to the experimental environment, those with almost uniform body weight values and no eye abnormalities were divided into the following 3 groups (n=4).

- 7 weeks old/normal (non-dry eye group)
- 7 weeks old/dry eye model+control (solvent eye drop) group
- 7 weeks old/dry eye model+apocynin eye drop group The dry eye model was prepared by dissolving erlotinib at a concentration of 5 mg/ml in 0.5% methylcellulose solution and administering it by intraperitoneal injection at a concentration of 50 mg/kg/day daily from the start of the study. The solvent 0.5% methylcellulose solution was similarly administered to the normal non-administration group. After one week of administration of erlotinib, the control group received PBS alone, and the test group received a solution of 0.003% (w/v) apocynin suspended in PBS twice a day at both eyes with 3 μL each. One week after the start of instillation, 1 μL of 0.1% sodium fluorescein solution was instilled into each of both eyes under isoflurane anesthesia, and the BUT test was performed under a blue filter using a slit lamp (Kowa Co., Ltd., SL-17) (FIG. 5).

Figure 5:
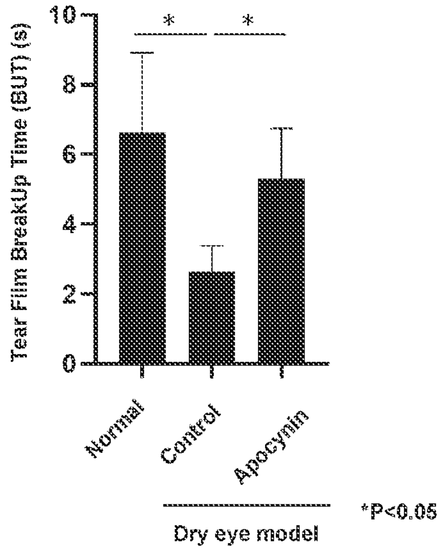
FIG. 5 It is a graph showing the results of tear film breakup time (BUT) in the dry eye model of Example 3. All error bars in the graph indicate S.D.

As shown in FIG. 5, BUT, which was significantly reduced by the systemic administration of erlotinib in the dry eye model, was significantly improved by instillation of apocynin, indicating that apocynin is useful as a tear film stabilizing agent.

Figure 6:
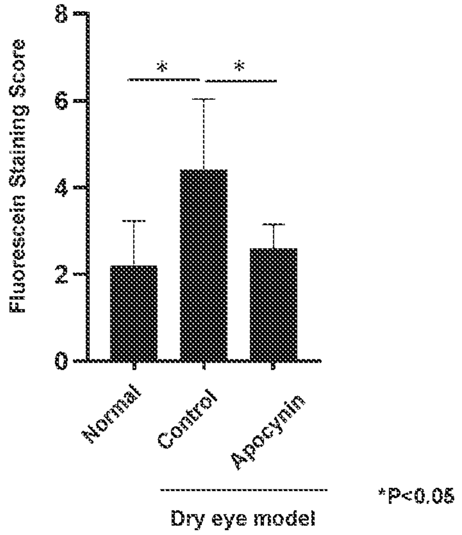
FIG. 6 It is a graph showing a fluorescein-stained image and staining scores in the dry eye model of Example 3. All error bars in the graph indicate S.D.

In Example 3, one week after the start of apocynin instillation, photographs were taken under isoflurane anesthesia, and the degree of corneal damage was scored (FIG. 6).

As shown in FIG. 6, corneal epithelial damage induced by systemic administration of erlotinib was significantly improved in the apocynin eye drop group, and it was shown that apocynin is useful as a therapeutic agent also for corneal epithelial damage in dry eye models induced by systemic drugs.

Evaluation of Therapeutic Effects on Meibomian Gland Dysfunction

Figure 7A:
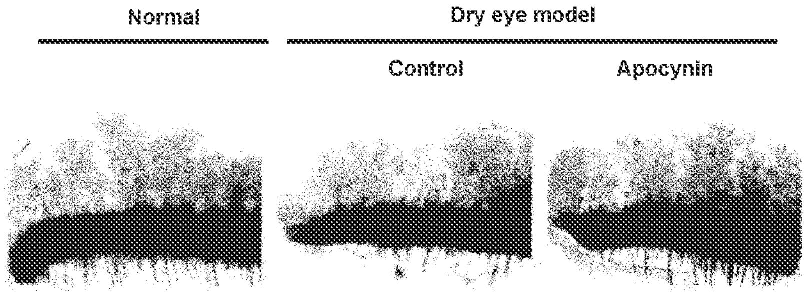
FIG. 7A It is a photographed image of an upper eyelid meibomian gland silhouette in the dry eye model of Example 3.

The mice used in Example 3 were sacrificed 2 weeks after the start of apocynin instillation, the skin and conjunctival epithelium of the upper eyelids were removed, and the silhouette of the meibomian glands was observed and photographed using a transmitted light source under a stereoscopic microscope. FIG. 7A shows a silhouette image of the upper eyelid taken from a dry eye model mouse. The areas that looked like dark shadows of trees were all meibomian glands. In addition, the image analysis software ImageJ was used to quantify the area of the meibomian gland silhouette image of the upper eyelid image (FIG. 7).

Figure 7B:
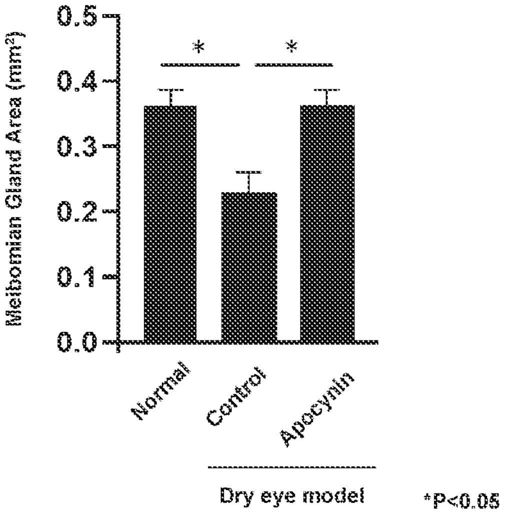
FIG. 7B It is a graph quantifying the meibomian gland area in the dry eye model of Example 3. All error bars in the graph indicate S.D.

As shown in FIG. 7, comparison of the silhouettes of the meibomian glands showed that some meibomian glands were missing in the dry eye model, and it was confirmed that the instillation of apocynin reduced the missing parts. Quantification of the meibomian gland silhouette area at this time revealed that apocynin significantly inhibits atrophy of the meibomian glands.

Therefore, it was shown that apocynin has the effect of improving the atrophy of the meibomian glands and is useful as a therapeutic agent for meibomian dysfunction.

Example 4: Therapeutic Effects of Apocynin on Dry Eye Model Animals (Comparative Study 1)

After acclimating male C57BL6 mice (7 weeks old) to the experimental environment, those with almost uniform weight values and no eye abnormalities were divided into the following groups (n=4).

- 7 weeks old/normal (non-dry eye group)
- 7 weeks old/dry eye model+control (solvent eye drop) group
- 7 weeks old/dry eye model+0.1% (w/v) apocynin eye drop group
- 7 weeks old/dry eye model+0.5% (w/v) hyaluronic acid eye drop group A dry eye model was prepared by instilling the benzalkonium chloride solution at 3 μL each eye, twice a day for 8 days. After that, the control group received the 0.5% methylcellulose solution alone, and the test group received 0.1% (w/v) apocynin or 0.5% (w/v) hyaluronic acid suspended in the 0.5% methylcellulose solution twice a day for 15 days at 3 μL for each of both eyes.

Schirmer's test was performed 1, 3, 6, and 8 days after the start of instillation of the comparative test drug, and tear volume was evaluated.

Figure 8:
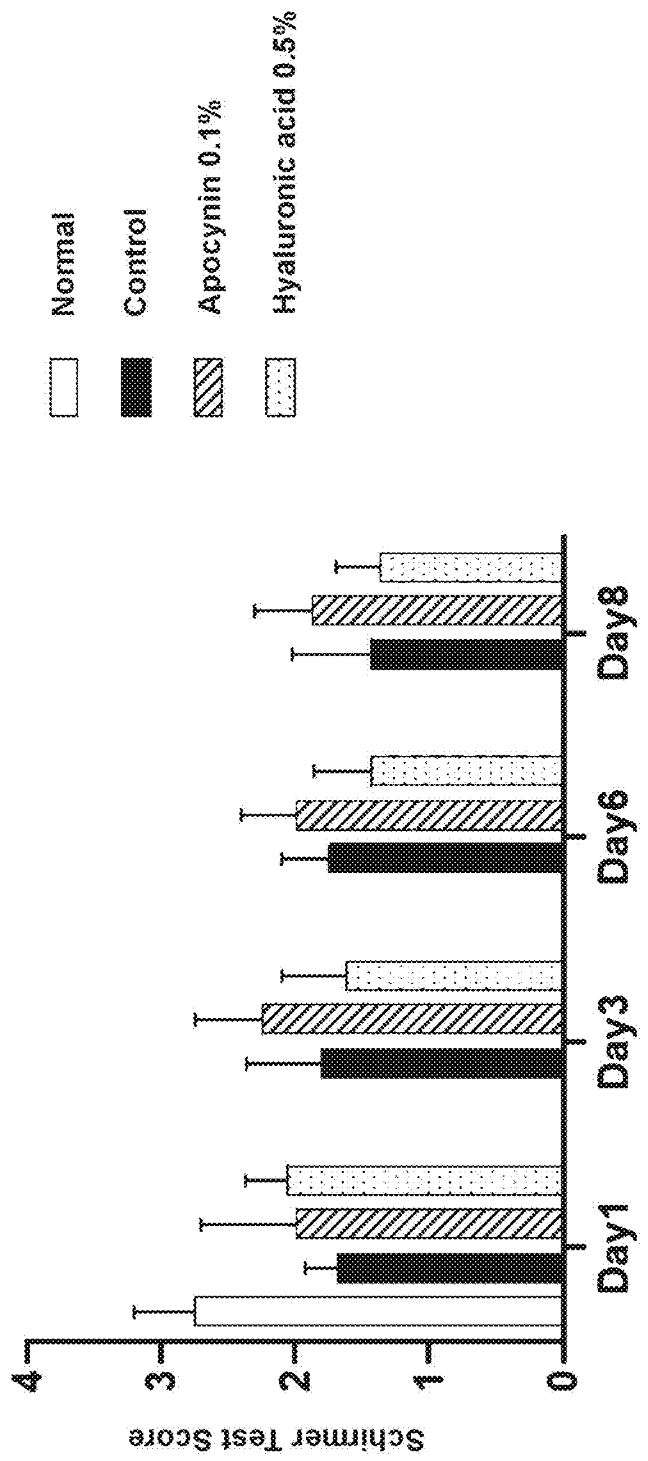
FIG. 8 It is a graph showing Schirmer test results in the dry eye model of Example 4. All error bars in the graph indicate S.D.

As shown in FIG. 8, in the dry eye model of Example 4, the control group showed a marked decrease in tear volume compared to the normal group. The apocynin eye drop group showed marked improvement in the tear volume compared to the hyaluronic acid eye drop group 3 days after the start of eye drop instillation. This suggests that apocynin is more effective than hyaluronic acid as a tear film stabilizer.

In Example 4, 1, 3, 6, 8, and 15 days after the start of instillation of the comparative test drug, 1 μL of the 0.1% fluorescein sodium solution was instilled into each of both eyes. Fluorescein-stained images were observed under a blue filter using a slit lamp (Kowa Co., Ltd., SL-17), and the degree of corneal epithelial damage was scored.

Figure 9A:
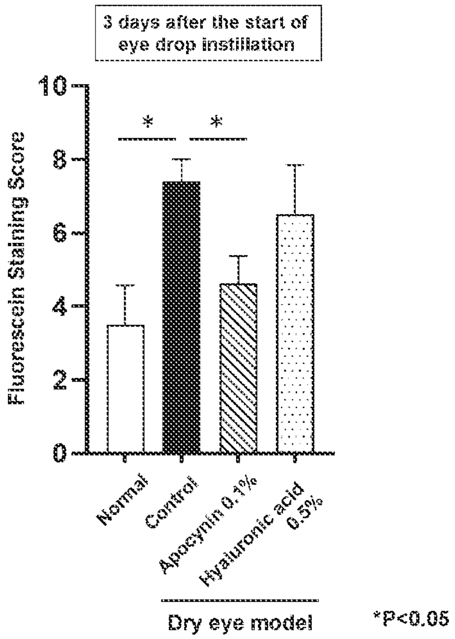
FIG. 9A It is a graph showing fluorescein staining scores in the dry eye model of Example 4. All error bars in the graph indicate S.D.
Figure 9B:
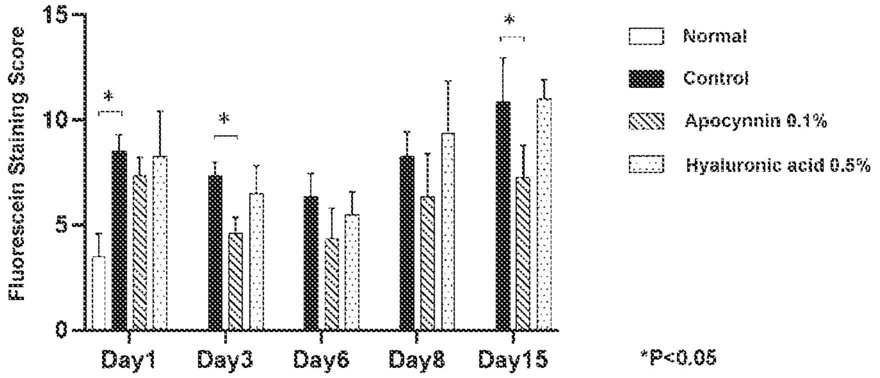
FIG. 9B It is a graph showing fluorescein staining scores in the dry eye model of Example 4. All error bars in the graph indicate S.D.

As shown in FIG. 9A, in the dry eye model of Example 4, the fluorescein staining score was significantly increased in the control group compared to the normal group, and corneal epithelial damage was observed. As shown in FIG. 9A, in the apocynin eye drop group, the fluorescein staining score was significantly reduced and the corneal damage was improved 3 days after the start of eye drop instillation compared to the control. On the other hand, no effect was observed in the hyaluronic acid eye drop group. Furthermore, as shown in FIG. 9B, in the apocynin eye drop group, a significant decrease in the fluorescein staining score was observed even 15 days after the start of eye drop instillation. From the above, apocynin has been shown to be more effective than hyaluronic acid as a therapeutic agent for corneal epithelial disorders.

Example 5: Therapeutic Effects of Apocynin on Dry Eye Model Animals (Comparative Study 2)

After acclimating male C57BL6 mice (7 weeks old) to the experimental environment, those with almost uniform weight values and no eye abnormalities were divided into the following groups (n=3 to 4).

- 7 weeks old/normal (non-dry eye group)
- 7 weeks old/dry eye model+control (solvent eye drop) group 7 weeks old/dry eye model+0.003% (w/v) apocynin eye drop group
7 weeks old/dry eye model+0.03% (w/v) apocynin eye drop group
7 weeks old/dry eye model+3% diquafosol sodium eye drop group
7 weeks old/dry eye model+0.5% (w/v) hyaluronic acid eye drop group A dry eye model was created by instilling 3 μL of the 0.2% benzalkonium chloride solution into each of both eyes twice a day for 8 days. Then, the control group received PBS alone, and the test group received 0.003% (w/v), 0.03% (w/v) apocynin and 0.5% (w/v) hyaluronic acid in PBS. The 3% diquafosol sodium eye drop was instilled into each of both eyes at 3 μL, twice a day for 9 days.

Two days after the start of instillation of the comparative test drug, the Schirmer test was performed to evaluate the tear volume.

Figure 10:
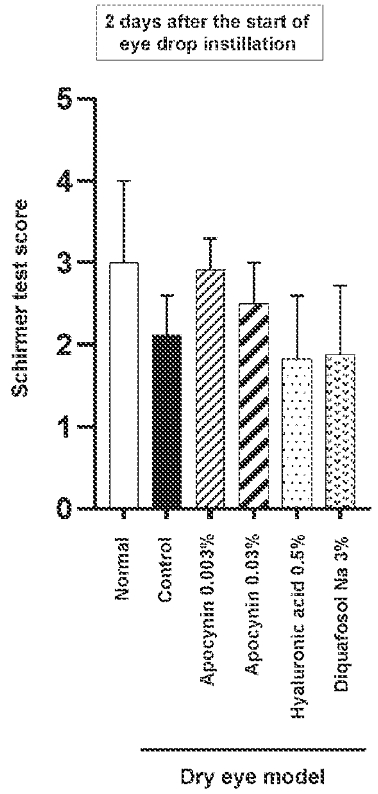
FIG. 10 It is a graph showing Schirmer test results in the dry eye model of Example 5. All error bars in the graph indicate S.D.

As shown in FIG. 10, in the dry eye model of Example 5, the control group showed a marked decrease in tear volume compared to the normal group. On the other hand, as shown in FIG. 10, in the 0.003% and 0.03% apocynin eye drop groups, 2 days after the start of eye drop instillation, tear volume was significantly improved compared to the hyaluronic acid eye drop group and the diquafosol sodium eye drop group. These results showed that apocynin is more effective than hyaluronic acid and diquafosol sodium as a tear film stabilizing agent.

In Example 5, 1, 2, 5, and 9 days after the start of instillation of the comparative test drug, 1 μL of 0.1% sodium fluorescein solution was instilled into each of both eyes. Fluorescein-stained images were observed under a blue filter using a slit lamp (Kowa Co., Ltd., SL-17), and the degree of corneal epithelial damage was scored.

Figure 11A:
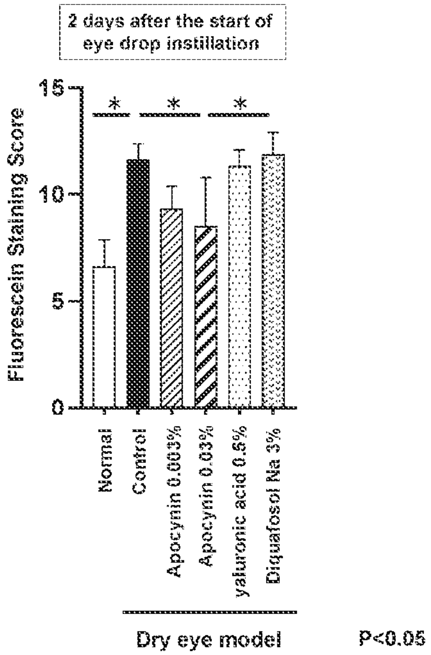
FIG. 11A It is a graph showing fluorescein staining scores in the dry eye model of Example 5. All error bars in the graph indicate S.D.
Figure 11B:
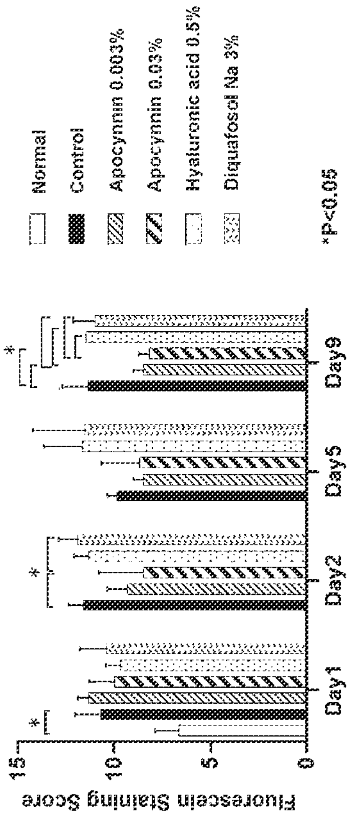
FIG. 11B It is a graph showing fluorescein staining scores in the dry eye model of Example 5. All error bars in the graph indicate S.D.

As shown in FIG. 11A, in the dry eye model of Example 5, the fluorescein staining score was significantly increased in the control group compared to the normal group, and corneal epithelial damage was observed. On the other hand, in the 0.03% apocynin eye drop group, the fluorescein staining score decreased significantly compared with the control group two days after the start of eye drop instillation, and amelioration of the corneal epithelial damage was observed. On the other hand, no effect was observed in the hyaluronic acid eye drop group and the diquafosol sodium eye drop group. Furthermore, as shown in FIG. 11B, 9 days after the start of instillation, the 0.003% apocynin and 0.03% apocynin eye drop groups significantly improved the fluorescein staining scores compared to the control group, the hyaluronic acid eye drop group, and the diquafosol sodium eye drop group. From the above, it was shown that apocynin is more effective than hyaluronic acid and diquafosol sodium as a therapeutic agent for corneal epithelial disorders.

In all types of dry eyes, whether the tear-deficient type, evaporative type, or short-BUT type, the primary outcomes of treatment are stabilization of the tear film (improvement of BUT shortening and tear fluid reduction) and reduction of corneal epithelial damage. In addition, improvement of the meibomian gland dysfunction leads to improvement of MGD which occurs in a significant proportion of dry eyes.

As shown in Examples 1 to 5, the apocynin of the present invention has a stabilizing effect on the tear film, a therapeutic effect on corneal epithelial damage, and a therapeutic effect on meibomian gland dysfunction, and has a remarkable prophylactic, ameliorating, or therapeutic effect on dry eyes of any of the tear-deficient type, evaporative type, and short-BUT type.

INDUSTRIAL APPLICABILITY

The therapeutic agent of the present invention, which has apocynin as an active ingredient, has been found to have a stabilizing effect on the tear film, a therapeutic effect on corneal epithelial disorders, and a therapeutic effect on meibomian gland dysfunction. Therefore, the present invention is useful as a prophylactic agent, an ameliorating agent or a therapeutic agent for dry eye.

The invention claimed is:

1. A method of treating a meibomian gland dysfunction in a subject in need thereof, the method comprising topically administering to an eye of the subject a topical ophthalmic composition comprising apocynin as an active ingredient, wherein the topical ophthalmic composition comprises the apocynin at a concentration of 0.001% (w/v) to 0.1% (w/v).

2. The method of claim 1, wherein the meibomian gland dysfunction is accompanied by atrophy of meibomian glands of the subject.

3. The method of claim 1, wherein the topical ophthalmic composition comprises the apocynin at a concentration of 0.003% (w/v) to 0.1% (w/v).

4. The method of claim 1, wherein the topical ophthalmic composition is an eye drop, an ophthalmic ointment, a patch, a gel, or an insert.

5. The method of claim 4, wherein the topical ophthalmic composition is an eye drop.

6. The method of claim 4, wherein the topical ophthalmic composition is an ophthalmic ointment.

7. The method of claim 4, wherein the topical ophthalmic composition is a gel.

8. The method of claim 2, wherein the method suppresses or ameliorates the atrophy of the meibomian glands.

9. The method of claim 8, wherein the administering of the topical ophthalmic composition inhibits a decrease in meibomian gland silhouette area.

10. The method of claim 1, wherein the topical ophthalmic composition further comprises an oily ingredient, a thickener, or a combination thereof.

11. The method of claim 6, wherein the ophthalmic ointment comprises white petrolatum, liquid paraffin, or a combination thereof.

12. The method of claim 1, wherein the topical ophthalmic composition further comprises one or more pharmaceutically acceptable additives selected from the group consisting of surfactants, preservatives, buffers, pH adjusters, stabilizers, polyhydric alcohols, and thickeners.

* * * * *